United States Patent [19]

Degler et al.

[11] Patent Number: 5,035,758
[45] Date of Patent: Jul. 30, 1991

[54] METHOD OF MAKING A BREAST PROSTHESIS

[75] Inventors: Peter Degler, Grassau; Bernhard Kramer, Marquartstein, both of Fed. Rep. of Germany

[73] Assignee: Kunststofftechnik Debler GmbH, Grassau, Fed. Rep. of Germany

[21] Appl. No.: 613,179

[22] Filed: Nov. 14, 1990

[30] Foreign Application Priority Data

Nov. 17, 1989 [DE] Fed. Rep. of Germany ....... 3938328

[51] Int. Cl.$^5$ ..................... B32B 1/10; B29C 39/12; A61F 2/52
[52] U.S. Cl. ................... 156/61; 156/272.2; 264/46.6; 264/511; 264/516; 264/222; 264/254; 264/267; 623/7
[58] Field of Search ............. 264/222, DIG. 30, 511, 264/512, 516, 46.6, 250, 254, 267; 623/7; 156/272.2, 61

[56] References Cited

U.S. PATENT DOCUMENTS 4,172,298 10/1979 Rechenberg ..................... 623/7 R
4,401,492 8/1983 Pfrommer ........................ 623/7 X

FOREIGN PATENT DOCUMENTS 3336279 2/1985 Fed. Rep. of Germany .

Primary Examiner—Jan H. Silbaugh
Assistant Examiner—Merrick Dixon
Attorney, Agent, or Firm—Townsend and Townsend

[57] ABSTRACT

A process for producing a breast prosthesis with a concave recess facing the human body. A synthetic resin composition curable to a gelatinous state is enclosed between two thermoplastic films and is shaped in a heated mold defined by a male die and female die. A first film which will face away from the human body is stretched over the female die and heated to permanently conform it to the contour of the die by deep drawing. The deep-drawn film is removed from the female die and an insert having a volume and a free area which correspond to the volume and free area of the concave recess facing the body is then positioned in the female die. The deep-drawn film is placed over the insert in the die and the die is filled with the synthetic resin composition up to its edge. The synthetic resin composition is covered with a second film (cover film) which is welded to the first film over these entire overlapping edges. The insert is removed, the second film is permanently shaped to the contour of the male die which corresponds to the shape of the concave recess and the synthetic resin composition is then cured with the help of a male die.

10 Claims, 1 Drawing Sheet

METHOD OF MAKING A BREAST PROSTHESIS

BACKGROUND OF THE INVENTION

Breast prostheses are used on a large scale after surgical removal of mammary carcinomas. They are usually made of a plastic composition, especially a synthetic silicone resin that cures to a gelatinous state, and the outer surface of the prosthesis is modeled to simulate the shape of the breast. Breast prostheses can be designed as either solid or hollow prostheses, but in the latter case the side of the prosthesis facing the body is hollowed out and has a concave configuration.

A distinction is made between film-free breast prostheses and prostheses sheathed in film. Film-free breast prostheses, which constitute only a small percentage of the prostheses currently on the market, have the disadvantage that they are tacky to the touch because the silicone resin composition often does not crosslink completely and uncrosslinked silicone oil seeps out.

In order to overcome this disadvantage, breast prostheses are sheathed with thermoplastic films, especially polyurethane films In general, such breast prostheses are produced by placing the uncrosslinked silicone resin composition together with the crosslinking agent and a catalyst between two flat films that form an envelope for the prosthesis. The films are welded together along this edge except for a small filling opening The films are then fixed at the edge of a cavity in the area of the welded edge in a die that corresponds to the shape of the breast. Silicone resin composition is added until the films are pressed against the walls of the die cavity, the film edges are then welded together in the area of the filling opening, and the silicone resin composition in the die at that point is crosslinked at an elevated temperature so it cures to form a gelatinous mass.

Breast prostheses of this type are described, for example, in German Patent Publications 2,701,627, 2,737,321 and 2,902,373.

However, welding the film edges together, especially in the area of the filling opening, poses problems when residues of the injected silicone resin composition are between the films. These residues prevent satisfactory welding of the film edges so the weld seam easily tears open and the silicone resin composition easily escapes during the curing process as well as after curing when even a slight pressure is applied to the prosthesis. Furthermore, the dies must be heated to a relatively high temperature (about 130° C.) in the welding and crosslinking operation and must be cooled between each step, which is very time consuming and expensive.

Another disadvantage of the welding process is that the welding electrodes applied to both films must fit precisely in order to produce a stable weld. This is practically possible only if the contacting surfaces are exactly flat. A breast prosthesis produced in this way is therefore flat on the side facing the body, so that undesirable folds develop when the prosthesis is positioned on the body.

Furthermore, known breast prostheses have only a low dimensional stability because of their natural softness and they can deform under their own weight if the dimensions of the prosthesis do not conform exactly to the dimensions of the brassiere.

In order to overcome these disadvantages, German Patent 3,336,279 proposes a breast prosthesis that consists of a synthetic resin composition cured to a gelatinous consistency and enclosed between two thermoplastic films welded together and composed of two layers of different strengths. This breast prosthesis is characterized in that the layer facing the human body has a higher strength and consists of condensation-crosslinked silicone resin. On top of this layer is a layer that faces away from the human body, has a lesser strength and is made of an addition-crosslinked silicone resin. The insides of the thermoplastic films have a layer of an adhesion promoter that is effective with respect to the condensation-crosslinked silicone resin at least in the areas of the edges.

According to the improvement for this prosthesis described in German Patent Application 3,416,240, the crosslinking temperature should be in the lower part of the plastic range of the film.

In producing this breast prosthesis, it is not necessary to leave an opening for injecting the curable synthetic resin composition. However, use of an adhesion promoting layer is necessary because the quantity of synthetic resin for producing the layer that faces the body cannot be metered precisely and yet it must be measured in such a way that the synthetic resin composition necessarily come to lie between the outer edge areas of the films. Furthermore, development of folds is often observed when producing such prostheses.

SUMMARY OF THE INVENTION

A purpose of this invention is to improve breast prostheses of this type in the sense of simplifying its production process. In particular, the filling of the breast prosthesis with the curable synthetic resin composition is to be improved while maintaining a dimensionally stable, concave shape facing the body, and finally, preventing a shifting of the two films during the production of the prosthesis and thus the development of folds.

This invention thus concerns a process for producing a breast prosthesis a. from a synthetic resin compound that is enclosed between two thermoplastic films and cures to a gelatinous state, b. with a cup-shaped recess in the prosthesis facing the human body, c. using a heated mold having a female mold and a male mold; which comprises the following steps:

1. A first film which is stretched taut and faces away from the human body is placed on the female mold, heated and permanently contoured to the shape of the mold by deep drawing (FIG. 1);

2. the deep-drawn first film is removed from the female mold;

3. an insert with a volume and a free area which correspond to the volume and area of the cup-shaped recess facing the human body is inserted into the female mold;

4. the deep-drawn first film is placed over the insert in the die (FIG. 2);

5. the female die is filled up to the edge with the synthetic resin compound;

6. the synthetic resin compound is covered with a second film that is then welded to the first film along their entire overlapping edges;

7. the insert is removed;

8. by using male mold, the second film is permanently contoured to the shape of the male mold which in turn corresponds to the shape of the cup-shaped recess in the prothesis facing the human body (FIG. 3); and 9. the synthetic resin compound is cured.

The term "free" area of the insert should be understood to refer to that area of the insert which is not in contact with the walls of the female die.

German Patent Application 2,126,587 relates to a process for producing multilayer articles of foamed plastic, but it makes no mention of doing so for breast prostheses. German Utility Patent 8,308,257 and German Patent Application 2,819,968 relate to breast prostheses, but they do not contemplate the use of an insert. German Patent 2,650,489 is concerned with the production of an air-filled interior space in a breast prosthesis; however, it does so without an insert and the use of an insert is nowhere mentioned.

In the process of this invention, the first film, which is preferably clamped in a frame, is permanently fitted to the contours of the female die before the synthetic resin composition is added. In this way, shifting of the film during the following process steps, and thus the development of folds, are prevented. The first film is preferably externally heated (e.g., by radiation or by hot air) to the softening point while the female die is kept at a temperature between the softening point of the film and the curing temperature of the synthetic resin composition. In this way, a constant production temperature can be maintained at all times. In accordance with the state of the art, the final shaping of the first film does not take place until the end of the hardening process because the softening temperature of the film is higher than the curing temperature of the synthetic resin composition. Due to the permanent deformation of the first film, another effect that is achieved is that the film can no longer be displaced during the subsequent operations.

This effect is increased by the use of the insert whose volume and free area correspond to the volume and area of the desired concavity facing the body. In this way, wrinkles or folds will not form after the film edges have been welded. It should be emphasized that it is not sufficient for the insert to have only the same volume, but not the same free surface area as the desired concavity. In such a case, the possibility of folding cannot be ruled out. The insert merely imparts an "indentation" to the deep-drawn first film. After removing the insert, the film returns to the shape it received as a result of deep drawing. In order to prevent the deep-drawn film from deforming, the insert is preferably inserted at a temperature below the softening temperature of the die. The temperature of the insert can be even below the temperature of the die. However, in any case the deep drawn film is placed tightly against the insert in the die so the effective volume of the insert enclosed by the second film corresponds to the volume of the concavity of the body.

The die is then filled with the synthetic resin composition up to the die edge. The edge of the die is in a plane so the die can readily be filled without requiring special equipment. A second or cover film is then placed over the synthetic resin composition. Since the synthetic resin composition extends up to the upper edge of the die, no air bubbles develop under the cover film while on the other hand the fact that the synthetic resin composition flows somewhat over the edge can be tolerated. However, it is better to allow the synthetic resin composition to harden somewhat superficially before applying the cover film, which can be accomplished, e.g., with radiation or with the help of hot air.

Thereafter the cover film is welded to the first film along their entire edges. In doing so, the film material can be welded directly to the other layer of film material, or welding can be accomplished by applying a layer of adhesion promoter to the edge of the lower film before welding.

Preferably the film edges are welded together by high frequency in which case the female die, which is made of metal, constitutes the first electrode and a metal plate placed over the cover film forms the second electrode.

After welding the insert is removed, in which case the first deep-drawn film inverts and adapts itself again to the contour of the female die. A recess that corresponds to the volume of the insert removed from the die is then formed in the synthetic resin composition. Displacement of the weld is impossible because the area of the "indentation" corresponds to the free area of the insert facing the synthetic resin composition.

The second film is then permanently contoured with the help of a male die which is shaped to the form the desired concavity in the side of the prosthesis facing the body. This can be accomplished by heating the cover film to the softening point with the help of the male die, or with a separate heat source before applying the male die. The second alternative is preferred so the temperature of the male die need not be varied between the softening point of the film and the curing temperature of the synthetic resin composition but instead can always be kept at the curing temperature of the synthetic resin composition.

After the synthetic resin composition is cured a breast prosthesis with a planar edge area is obtained. If the breast prosthesis is to be shaped further, the still uncured breast prosthesis is placed in another mold with an edge that is not flat and whose contour preferably has been fitted to the contour of the body surface and the synthetic resin composition is cured in this mold.

Furthermore, several layers of synthetic resin compositions with different properties yielding different strength characteristics after curing can be used, in which case the second and optionally subsequent layers are preferably inserted when the first layer and the layer inserted before it are cured at the surface. The first layer can be selected so that when cured it corresponds in color and/or hardness to the nipple of a breast. Then as indicated in German Patent 3,336,279, the following layer may be somewhat softer in the cured state and may be made, for example, of a silicone resin composition that is cured by addition crosslinking. Furthermore, a layer that has an even greater strength after curing can also be added. For example, a silicone resin that crosslinks by condensation can be used for this purpose.

The breast prosthesis of this invention will thus retain its natural softness, which is due to the lower strength of the second layer of the addition-crosslinked silicone resin composition, whereas on the other hand it will have a good dimensional stability due to the greater strength of the third layer of the condensation cross-linked silicone resin, making it possible for the surface of the prosthesis, which is next to the body, to be permanently curved to conform to the body's contours without resulting in any folds as would be the case with a breast prosthesis with a flat contact area.

The required dimensional stability is also promoted by the fact that the somewhat more solid silicone resin composition of the third layer acts as a binder between the thermoplastic films, in which case the thermoplastic films, especially the first film, also contribute toward an increase in dimensional stability. The thickness of the third layer is usually at least 2 mm, preferably at least 4 mm.

There are no particular restrictions with regard to the thermoplastic films. They must only have a certain extensibility at room temperature or in the heated state and they must bond to the more solid condensation-crosslinked silicone resin composition. Practically any films that are suitable for the deep drawing process can be used. However, the films are preferably based on polyurethane.

With the addition-crosslinked resins, the crosslinking agent reacts with the reactive parts of the silicone resin chains without generating smaller molecules as is the case when silicone resin is condensation-crosslinked. Addition crosslinked and condensation-crosslinked silicone resin compositions are well known, thus, they are not further discussed here (see, for example, the German language periodical *Chemiker-Zeitung*, 97 (1973) pages 176-180).

The required dimensional stability of the breast prosthesis of this invention is due mainly to the tensile strength of the cured silicone resin composition of the third layer and the tensile strength of the thermoplastic films bonded to this silicone resin composition. The tensile strength of the silicone resin composition is usually at least 0.05 $N/mm^2$, and preferably 0.08 to 0.15 $N/mm^2$. The cured silicone resin compositions usually have a Shore hardness (according to DIN standard 33,505) of about 0.2 to 15, preferably about 0.1 to 1 (measured with a 45° plastic cone, 15 g).

On the other hand, the tensile strength of the cured silicone resin composition(s) of the layer(s) facing away from the body is much lower, so this layer/these layers determine(s) the required softness of the breast prosthesis. The tensile strength of these silicone resin compositions could not be measured according to the DIN method described above.

The silicone resin compositions used according to this invention can be cured with the help of the usual curing agents, typically by heating. For this purpose, the male and female dies used to produce the breast prostheses are typically heated electrically, e.g., with electric resistance heating elements. Heating can also be accomplished with the help of a hot fluid medium that flows through heating channels in the male and female dies.

In general, temperatures of about 60 to 90° C. are used to cure silicone resins. The temperature required for curing depends on various factors such as the type of resin and the crosslinking agent, the quantity ratios of these components as well as the type and concentration of the catalyst used for curing.

A special advantage of the process of to this invention is that the temperature of the male and female die molds can be kept constant, i.e., cooling is not necessary when raising the deep-drawn first film for insertion of the insert and for removal of the finished breast prosthesis. This results in substantial savings of time and costs.

The synthetic resin compositions used according to this invention may contain various additives, e.g., fillers, dyes, catalysts, etc. Preferably the synthetic resin compositions are generally dyed to conform to the natural skin color.

Furthermore, air-filled chambers or areas of some other material (e.g., a foam) can also be provided in the synthetic resin composition in order to vary the weight and/or the strength of the breast prosthesis.

DESCRIPTION OF THE PREFERRED EMBODIMENTS

Figure 1:
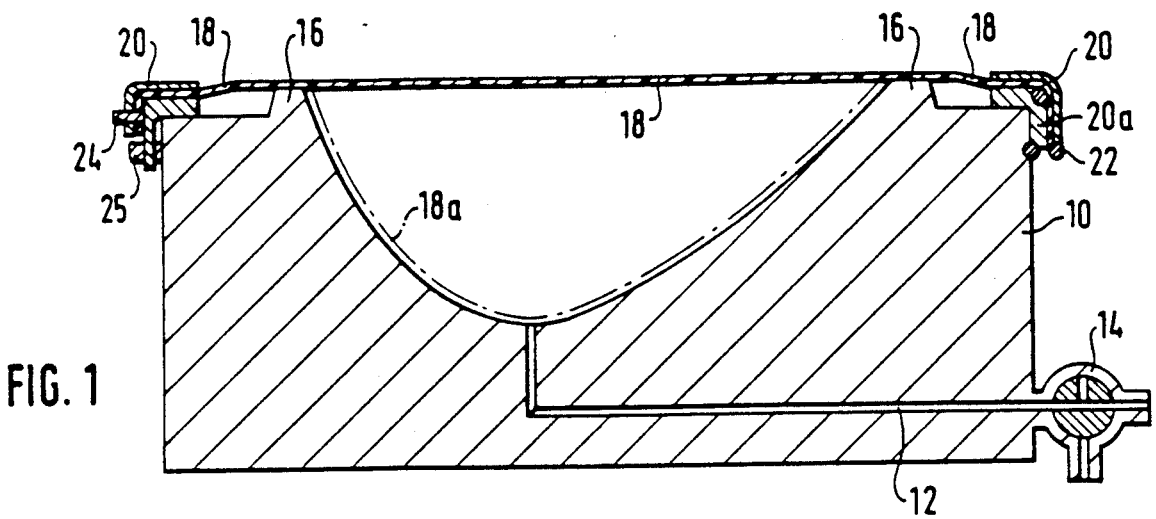
FIG. 1 shows the deep drawing of the first film.

Female die 10 can be heated to a temperature of 90° C, for example, by means of electric heating elements (not shown). It has a cavity that is shaped to correspond to the outer shape of the breast. A vacuum line 12 connected with a valve 14 outside the die opens into the lower part of the die cavity so that a vacuum can be applied. The cavity of the die is bordered by a flat edge or rim 16.

To produce the prosthesis, a first thermoplastic film 18 is initially stretched over the heated female die 10 and clamped with the help of frame 20. A hinge 22 connects the frame to a base frame 20a and a lock 24 releasably secures the frame. Film 18 is thus stretched from the cavity of the die to the rim 16 or slightly beyond.

After securing film 18, it is heated with the help of a radiant heater or with hot air to its softening point (about 130° C. in the case of thermoplastic polyurethane film) and vacuum valve 14 is opened. Film 18 is thereby deep drawn and conforms to the wall of the cavity of die 10, i.e., it is converted into a shell which has the shape of the breast (indicated with 18a in FIG. 1). Since the temperature of female die 10 is below the softening point of film 18, the latter solidifies and retains its form even when the vacuum is released by closing valve 14. The deep-drawn film 18a clamped in frame 20 is then removed from the die cavity by releasing lock 25 and lifting base frame 20a so that insert 26 can be placed in the cavity. The insert has a volume VI which corresponds to the volume V2 of the concavity facing the body. Its production is described below in detail. The free surface area of the insert, i.e., the area that is not in contact with the wall of the cavity (indicated by the dotted line "a" in FIG. 2) corresponds to the area of the volume $V_2$ (indicated by the dotted line "b" in FIG. 3).

Figure 2:
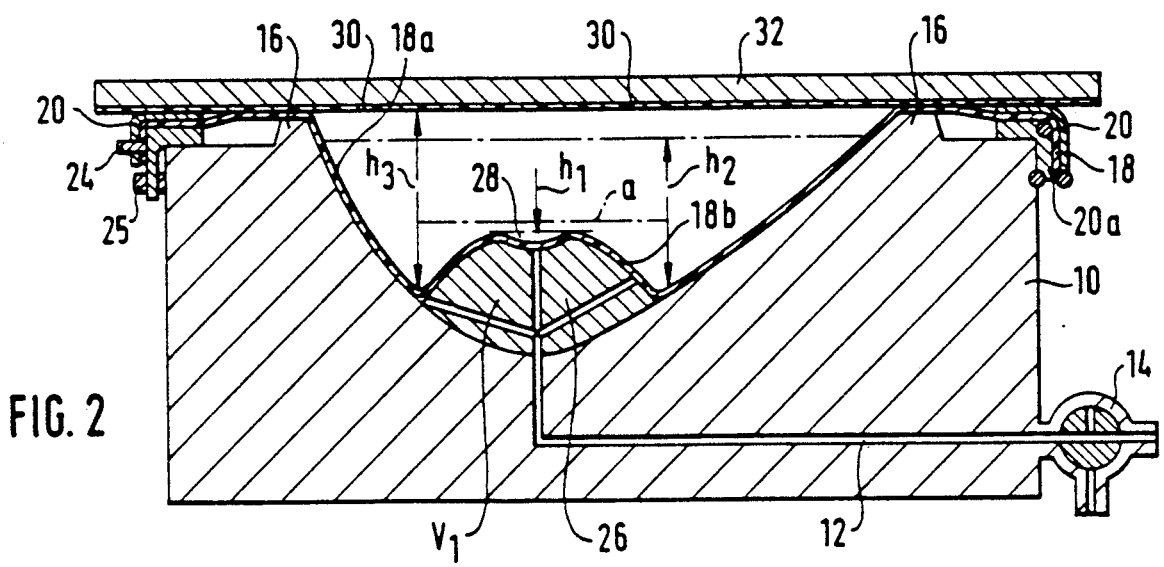
FIG. 2 shows the insertion of the insert and welding the cover film to the first film.

Insert 26 can have a small recess 28 in the middle into which the synthetic resin composition, which yields the nipple of the breast after curing, is added up to level "hl" (shown in FIG. 2).

After positioning insert 26 in the cavity (FIG. 2), the deep drawn film 18a held by base frame 20a is inserted back into the recess of female die 10. Its center is pressed upward and thus indented (indicated by 18b in FIG. 2) but otherwise retains its shape because the temperature of the insert 26 is below the softening point of the film. Valve 14 is then opened and a vacuum is again applied so the film is pressed tightly against the insert in the area 18b. The synthetic resin composition which yields the nipple of the breast after curing is now added into the recess 28 up to level $h_l$ and cured superficially by applying radiant heat or hot air.

Next the remaining synthetic resin composition is inserted up to die rim 16 either as one layer or as a plurality of layers of different compositions. Thus, for example, first a layer of addition-crosslinkable silicone resin may be added up to level $h_2$ (FIG. 2) and then a layer of condensation-crosslinkable silicone resin is added up to level $h_3$, i.e., up to the height of rim 16. In order to prevent the individual layers from mixing, the lower layer in each case can be superficially hardened by radiant heat or hot air before adding the next layer.

Cover film 30 is then stretched over female die 10, during which time it comes in contact with film 18 at die edge 16.

A flat metal plate 32 that serves as the high frequency welding electrode is placed over cover film 30 so that it can be welded to film 18 along edge 16. The metallic edge 16 of die 10 serves as the second high frequency welding electrode.

Figure 3:
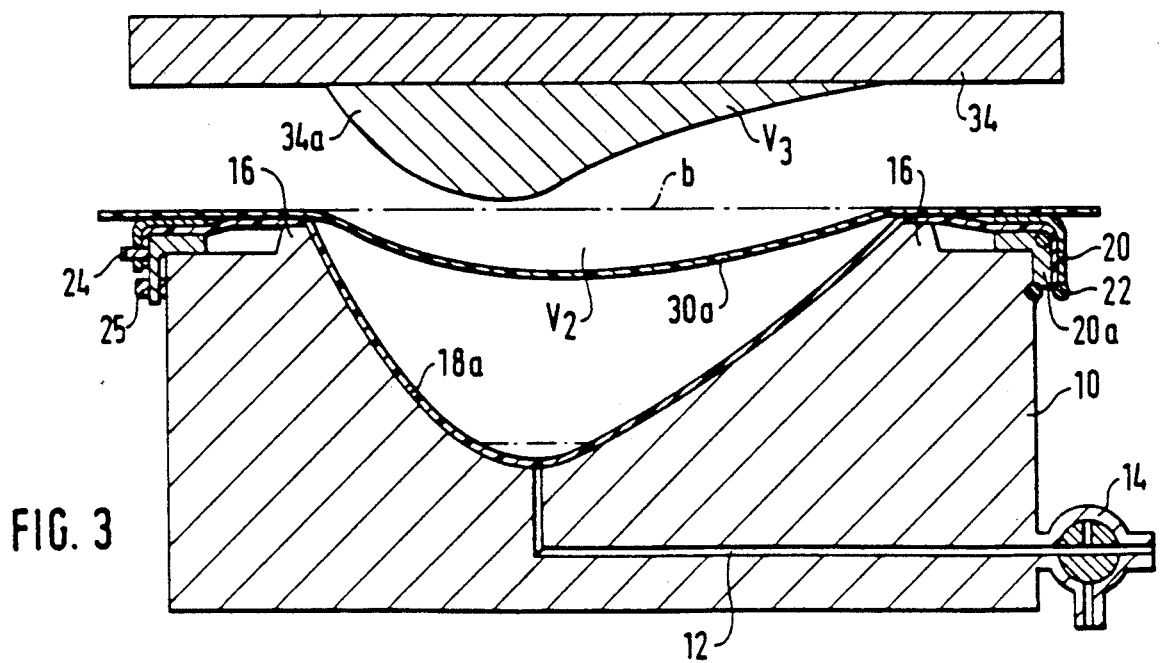
FIG. 3 shows the desired concavity of the prosthesis facing the body and the male die used to obtain it.

After welding together films 18 and 30, metal plate 32 is removed, base frame 20a is raised and insert 26 is removed from the recess. The area of film 18 labeled as 18b then folds (FIG. 3) into the position indicated with 18a, taking with it all the added synthetic resin composition. At the same time film 30 is heated by radiant heat or hot air so it is lowered into the position indicated by 30a (FIG. 3).

It can be seen here that no tension is applied to film 18 at edge 16, so the weld seam is not displaced.

The contact between the film and the wall of the cavity of female die 10 in area 18a is promoted by creating a vacuum. Finally, a male die 34, which is heated by heating elements (not shown) like female die 10 is also applied. Male die 34 has a curvature 34a whose volume corresponds to the volume of the concave shape facing the body and thus also corresponds to the volume $V_1$ or $V_2$. The temperature of the male die curvature 34a may be somewhat higher than the temperature of female die 10 if film 30 has not previously been subjected to thermoplastic deformation or if thermoplastic shaping has been incomplete. After curing the synthetic resin composition by heating with female die 10 and male die 34 (especially curvature 34a) the vacuum is broken and the cured breast prosthesis is removed from the recess of die 10 by lifting frame 20 and it is then cut along the edge 16.

If a breast prosthesis whose contour conforms to the contour of the body surface is desired as described in German Patent 3,336,279, the as yet uncured breast prosthesis is placed in a different female die shape with a correspondingly shaped edge that is not flat (after welding film 30 to film 18) and a heated male die with a correspondingly shaped edge that is also not flat is placed on top of it so the top layer of the synthetic resin composition which faces the body is cured first in this other mold.

What is claimed is:

1. Process for producing a breast prosthesis having a concave recess facing the human body from a synthetic resin composition that can be cured to a gelatinous consistency in a heated mold including a female die and a cooperating male die and that is enclosed between first and second thermoplastic films, the method comprising the steps of:
    a. clamping a first film which defines a side of the prothesis facing away from the human body to the female die, heating and deep drawing the first film to permanently conform it to the contour of the female die;
    b. removing the deep-drawn first film from the female die;
    c. placing an insert into the female die, the insert having a volume and a free area which correspond to the volume and a free area of the concave recess facing the human body;
    d. positioning the deep-drawn first film in the female die and in conformance with the insert;
    e. thereafter filling the positioned deep-drawn first film in the female die to about an edge of the die with the synthetic resin composition;
    f. covering the synthetic resin composition with a second film and welding together the first and second films along their entire overlapping edges;
    g. removing the insert from the female die the first film again taking the contour of the female die;
    h. permanently imparting to the second film the concave recess with a corresponding contour of the male die; and
    i. curing the synthetic resin composition to produce the breast prosthesis.

2. Process according to claim 1, including the step of heating the first film to its softening temperature with an external heat source before the deep drawing step and maintaining the female die at a temperature between the softening temperature of the first film and the curing temperature of the synthetic resin composition.

3. Process according to claim 1, wherein the insert has a temperature below the softening temperature of the first film.

4. Process according to claim 1, wherein the step of welding the film edges together comprises high frequency welding and wherein the female die forms a first welding electrode and a metal plate placed over the second film forms a second welding electrode.

5. Process according to claim 1, wherein, prior to the imparting step, the second film is heated to the softening temperature with one of the male die and an external heat source, and wherein the step of imparting includes positioning the male die over the second film.

6. Process according to claim 1, including the step of surface curing the resin composition in the female die prior to the step of covering the composition with the second film.

7. Process according to claim 1, including, prior to the curing step, the step of placing the breast prosthesis in a different mold having a non-planar edge and whose contour corresponds to the contour of the human body surface, and curing the synthetic resin composition in the different mold.

8. Process according to claim 1, including the step of filling the female die with several layers of synthetic resin compositions having differing properties, each layer being added after the preceding layer has been surface cured.

9. Process according to claim 8, including the step of coloring the first layer so that, after curing, it corresponds in color and/or hardness to the nipple of a breast.

10. Process according to claim 1, including the step of incorporating one of an air-filled chamber and another material in the synthetic resin composition.

* * * * *